United States Patent [19]

Taranowski et al.

[11] Patent Number: 5,229,841
[45] Date of Patent: Jul. 20, 1993

[54] COLOR SENSOR EMPLOYING OPTICAL FIBER BUNDLES WITH VARIED DIAMETERS

[75] Inventors: Michael G. Taranowski, Milwaukee; David L. McClanahan, South Milwaukee, both of Wis.

[73] Assignee: Eaton Corporation, Cleveland, Ohio

[21] Appl. No.: 727,730

[22] Filed: Jul. 10, 1991

[51] Int. Cl.⁵ .................. G01N 21/25; F21V 7/04
[52] U.S. Cl. ..................... 356/406; 362/32; 356/407
[58] Field of Search ............ 356/402-411, 356/326, 328; 385/12; 362/32, 231, 800

[56] References Cited

U.S. PATENT DOCUMENTS

| | | | |
|---|---|---|---|
| 3,885,879 | 5/1975 | Louder et al. | 356/326 |
| 4,131,367 | 12/1978 | French et al. | 356/405 |
| 4,464,054 | 8/1984 | Karras et al. | 356/406 |
| 4,564,261 | 1/1986 | Kojima et al. | 350/96.24 |
| 4,653,014 | 3/1987 | Mikami et al. | 364/526 |
| 4,815,816 | 3/1989 | Schneider | 350/96.25 |
| 4,917,500 | 4/1990 | Lugos | 356/406 |
| 5,000,569 | 3/1991 | Nylund | 356/237 |
| 5,011,261 | 4/1991 | Gordon | 350/96.25 |

OTHER PUBLICATIONS

Malone, "An In-Line Sensor for Color Monitoring and Control in the Food Industry," HunterLab.
McFarlane, "On Line Color Measurement," Ceral Foods World, Jun. 1985, vol. 30, #6, pp. 386-388.
Juds, "Photoelectric Sensors and Controls," Optical Fundamentals, Chapter 2, p. 59.

Primary Examiner—F. L. Evans
Assistant Examiner—K. P. Hantis
Attorney, Agent, or Firm—L. H. Uthoff

[57] ABSTRACT

A device (1) for photoelectrically sensing the color of an object (18) includes a plurality of light emitting diodes (4, 6, 8) emitting light in a narrow range of wavelengths and where the light is transmitted through a corresponding fiber optic bundle (10, 12, 14) with a diameter in proportion to the transmission loss of the bundle and in inverse proportion to the emitted light energy of the corresponding light emitting diode and in proportion to the spectral response of a receiving photodiode (24). A receiving section (22) utilizes a PIN type photodiode (24) with an input section (40) that matches the shape of a receiving optical fiber bundle termination (42) where the photodiode (24) converts the reflected light from the object (18) into electrical signals which are then processed by a microprocessor (28) which also controls the activation of the light emitting diodes (4, 6, 8) and outputs a signal indicative of the color of the object (18).

18 Claims, 6 Drawing Sheets

COLOR SENSOR EMPLOYING OPTICAL FIBER BUNDLES WITH VARIED DIAMETERS

BACKGROUND OF THE INVENTION

1. Field of the Invention

The present invention relates to a color sensor system for the recognition of objects and surfaces that are at least partially colored.

2. Description of the Prior Art

Color is a very important factor in maintaining the overall quality of food products and manufactured goods. Because the color of a product is often equated to quality, it is highly desirable to be able to control the product processing based on a color measurement to maintain consistency and adhere to specified product standards. By incorporating a color sensing system on the production line, more products can be monitored than with recognized off-line measurement techniques. Currently available color sensor technology has a number of deficiencies, limiting application thereof in many areas.

In one prior art color recognition system, the object to be analyzed for color content is illuminated with a white light, for example, the light from a halogen lamp can be used. The reflected light from the object is analyzed by means of lenses and standard color filters to split the reflected light into the primary colors, red, green and blue. The intensity of the individual color components is then converted into electrical signals by photo sensors, one for each color, which are connected to receiving amplifiers. One example of such a photo sensor is a light sensitive photodiode. In these systems, the transmitting light generator and the light receiver and amplifiers are located in close proximity to the object or the surface to be color analyzed which is often a problem in many food processing or manufacturing operations. Also, halogen light sources have a relatively short life span and shutdown of the production line is required for replacement.

For longer life, LEDs can be used as a light source. In another prior art color recognition system, the object to be analyzed for color content is illuminated with the light emitted by a plurality of light emitting diodes (LEDs) where each diode emits light energy in a narrow-band range of wavelengths. Commonly, LEDs emitting red, green and blue colored light are used for illumination. The reflected light from the object is then analyzed for color content.

Separate LEDs are used for orange (or red), green and blue light all of which emit different amounts of light energy. Again, the color measurement of the object is affected by the imbalance of the LED light energy that is used to illuminate the object whose color is to be analyzed and the imbalance of the spectral response of the receiver. LEDs and sensors which are used on-line frequently have their sensing heads and light source and processing logic separated by bundles of fiber optic cables wherein the termination of the transmitting and receiving end of the fiber optic cable is positioned closely spaced from the object while the other components are physically remote to protect them from the manufacturing process or to overcome space limitations.

A modulated color sensor system is known which has a plurality of electronic light transmitters (e.g. LEDs) emitting light of various wavelengths which, in succession, briefly illuminate an object whose color is to be determined with light pulses. The light reflected from the object is directed to a photo sensor, which converts the light signals into electrical signals for eventual evaluation for color content. By using a threshold light indicator (checking each color in succession) no provision is made for a quantitative evaluation of the intensity of the individual color components, such as is necessary for a determination of mixed colors and the result is an inaccurate color spectrum.

U.S. Pat. No. 4,917,500 the disclosure of which is incorporated herein by reference, describes a color sensor system that accounts for the relative intensity of the individual color components. The system employs at least three light emitting diodes (LEDs) emitting light pulses in a predetermined narrow-band range of wavelengths and an identical transmitting optical fiber bundle associated with each LED. A light receiving optical fiber bundle is packaged with the transmitting optical fiber bundles so that the reflected light from the colored surface of the object is transmitted through the optical fiber bundle to a light receiver having a photo semiconductor. The optical fiber bundles can be assembled together in one sensor head. The problem with this system is that for a given signal to noise ratio, the size of the sensor head is not minimized.

SUMMARY OF THE INVENTION

In accordance with the principles of the invention, a color sensor system is provided for recognition of the color of the surface of an object, comprising at least three electronic light emitters, emitting light in a predetermined narrow-band range of wavelengths; at least three optical fiber bundles with diameters inversely proportional to the light energy emitted from each of the electronic light emitters and proportional to the transmission loss through the respective optical fiber bundles and inversely proportional to the optical sensitivity of a receiving photodiode; a receiving optical fiber bundle that relays the reflected light from the object to an electronic light receiver for receiving light reflected from said colored surface and converting the reflected light into individual electrical signals having intensity corresponding to that of said reflected light. The receiver uses a photodiode where the shape of the end of the receiving optical fiber bundle matches the input section of the photodiode. Optical lenses can be used to focus the light transmission to customize performance.

The invention has the advantage that a color measurement of high precision can be made where the measured orange, green, blue reflectivity accurately indicates the actual reflectivity of the object. The present invention allows a more efficient use of fiber bundles by adjusting for any difference in LED light energy output by utilizing transmitting fiber optic bundles where the bundle diameter is sized to increase the amount of light transmitted from the lower power LED (i.e., the largest diameter optical fiber bundle is used to transmit the light from the blue LED which has the lowest light energy output). In addition, the difference in the response of the light detector in the receiver (known as its spectral response), which varies with the wavelength of the inputted light is considered for sizing purposes along with the LED output. Thus, using the present invention, the optical fiber bundle is sized according to the LED output in addition to the light detector spectral response so that the output signal from the light detector (photodiode) is equalized for each of the reflected illuminating colors (orange, green and blue) when a Kodak Whitecard is measured.

Another advantage of the present invention is that the termination end of the receiving optical fiber bundle is shaped to match the input section of the photodiode located in the receiver section so that the light incident on the detector is maximized thereby improving the signal to noise ratio.

Accordingly, it is an aspect of the present invention to provide a color sensor system by means of which an accurate color determination of an object can be made with a high degree of spectral accuracy where the receiver and transmitter can be remote mounted with the light signals being relayed through the use of selectively sized optical fiber bundles so as to optimize the overall system transfer function while minimizing the overall size of the fiber optic cable and sensing head.

Another aspect of the present invention is to provide a color sensor with a high signal to noise ratio.

Still another aspect of the present invention is to provide a color sensor such that when a calibrated object such as Kodak Whitecard is measured, the signal generated at the receiver photodiode is equalized for each of the illuminating colors so as to maximize the dynamic range of the system.

Still another aspect of the present invention is to provide a color sensor that can conveniently and effectively measure the color characteristics of a fluid.

Other features and advantages of the invention will be apparent from the description of the preferred embodiments, and from the claims.

For a more complete understanding of the present invention, reference should now be made to the following detailed description of the preferred embodiment of the invention and to the drawings.

DETAILED DESCRIPTION OF THE PREFERRED EMBODIMENT

Figure 1:
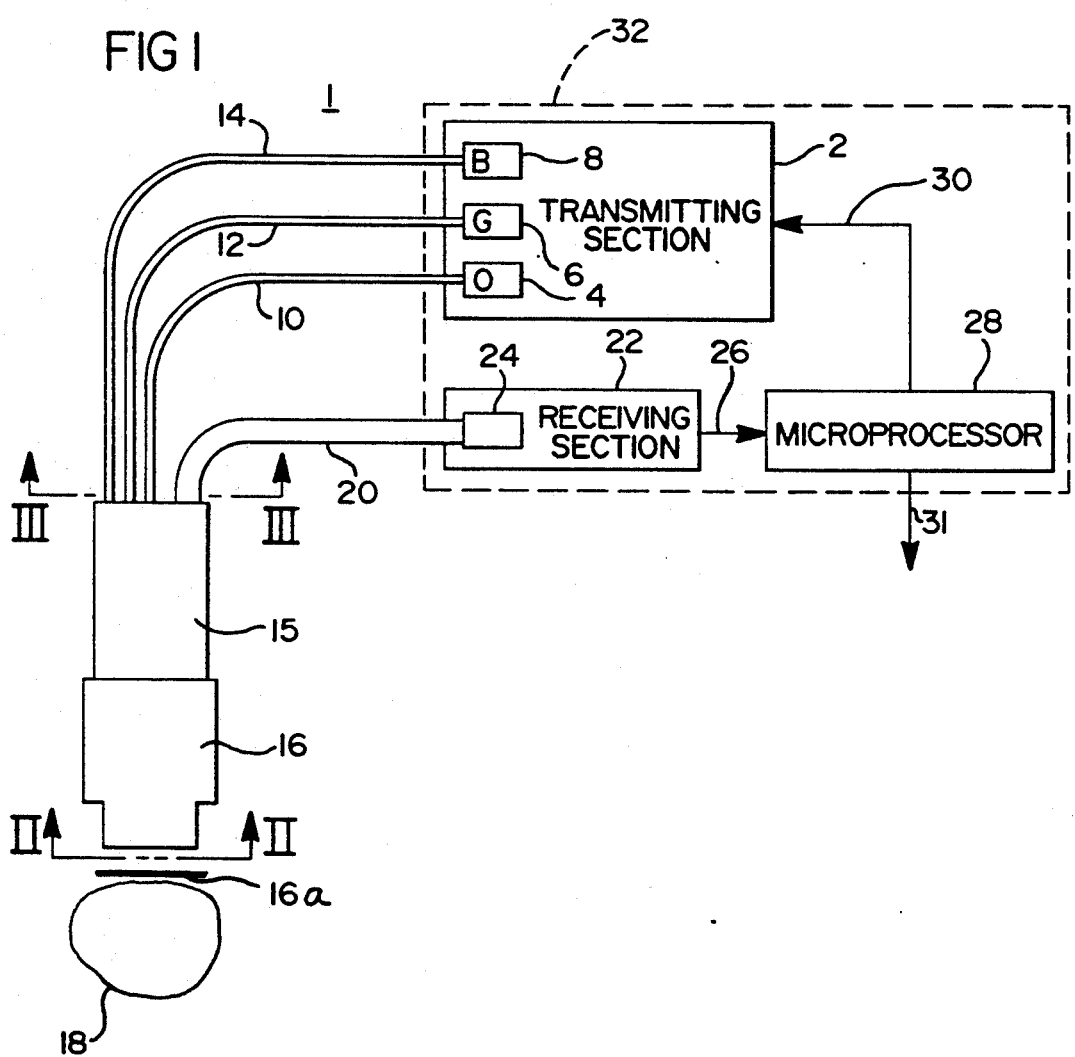
FIG. 1 illustrates a block schematic diagram of a color sensing system according to the present invention.

FIG. 1 illustrates a block schematic diagram of a color sensor system 1 of the present invention. It consists of a transmitting section 2 which includes a plurality of light emitting diodes (hereinafter LEDs) 4, 6, and 8 which emit light in a predetermined narrow-band range of wavelengths such as those known as Stanley Hi-Superbright LED, Orange 605, Part No. HAA5066X, Pure Green 555, Part No. HBG5066X, and in addition, Blue 470 manufactured by CREE Research. The dominate wavelengths selected are as follows: LED 4—605 nm, LED 6—555 nm, and LED 8—470 nm. Each LED is connected to a bundle of optical fibers so that the emitted light from each individual LED 4, 6, or 8 is directed into an individual respective transmitting optical fiber bundle 10, 12, or 14. The LED 4 (orange) is connected to optical fiber bundle 10 which has a small diameter and LED 6 (green) is connected to optical fiber bundle 12 which has a medium diameter and LED 8 (blue) is connected to optical fiber bundle 14 which has a large diameter. Transmitting optical fiber bundles 10, 12 and 14 and receiving optical fiber bundle 20 are separate as they leave the transmitting section 2 and receiving section 22 respectively, but are then joined at one end to form one system bundle 15. Within the system bundle 15, the individual optical fiber strands that make up each of the bundles 10, 12, 14 and 20 are intertwined and randomized and terminated at the other end of the system bundle 15 at the sensing end 16. Sensing end 16 with lens 16a directs the transmitted light from the LEDs 4, 6, and 8 onto an object 18 with a colored surface thereby illuminating the object 18 and can be positioned near the object 18 while the balance of the system is remote mounted. The illuminating light is reflected off object 18 where it is picked up by receiving optical fiber bundle 20 and is relayed back into receiving section 22. Specifically, the reflected light is directed into a light sensitive photodiode 24 where an electrical signal indicative of the level of light reflected by the object 18 is generated. The electrical signal is then relayed through line 26 to a controller/microprocessor 28 where the electrical signal is interpreted and used to control a process of some type. The controller/microprocessor 28 uses software to not only process the color electrical signal, but also generates a control signal that is transmitted via line 30 which regulates the operation of the transmitting section 2.

Figure 6:
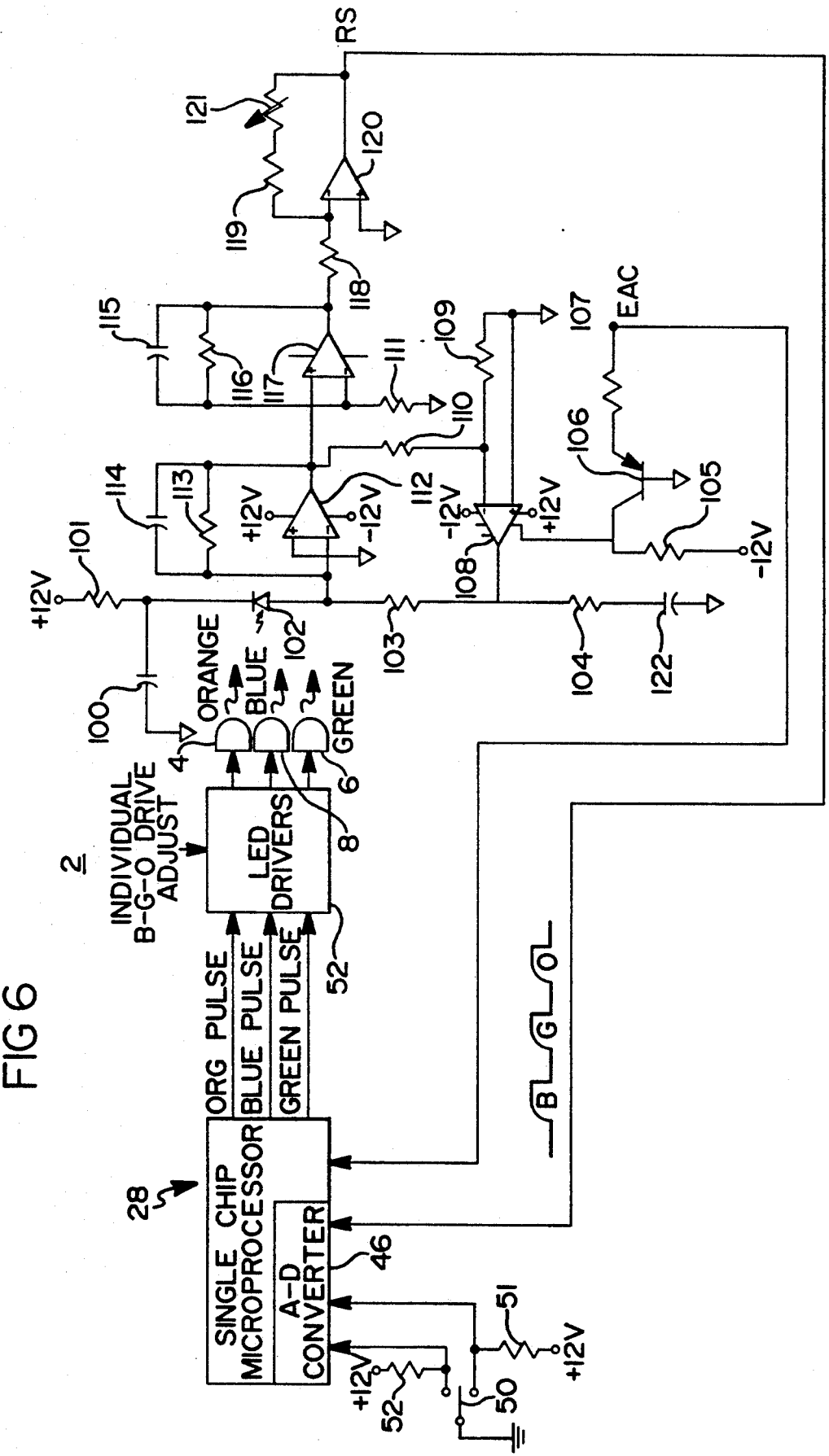
FIG. 6 illustrates a schematic diagram of a preferred embodiment of the present inventive photoelectronic color sensor.

Referring to FIG. 6, LEDs 4, 6, and 8 are sequentially triggered by microprocessor 28 and powered by driver circuit 52 to illuminate object 18 with orange, green and blue light as illustrated. The reflective light from each color is detected by photodiode 102, and amplified by operational amplifiers 112, 117 and 120, respectively. Op amp 120 outputs resultant sample signals to A-D converter 46 within microprocessor 28.

Now, described more specifically is the design and operation of the color sensing electronics and the algorithm used to control the operation of the LEDs and to determine the color spectrum. Referring to FIG. 6, microprocessor 28 generates timing pulses for the orange, green and blue LEDs 4, 6, and 8, respectively, and in synchronism with each pulse, samples the output of op amp 120 and converts it to a digital value. These digital values for each color are stored in memory and may be processed with any of several algorithms to determine the color of the target being viewed. One such known algorithm or conversion relationship is known as Munsell equations which describes an exact color by way of a vector on a circle with its origin at the center of the circle. Alternatively, the orange, green and blue values may be compared to a stored set of colors obtained by viewing a reference color during a "learn" mode at set-up. This is functionally described in FIG. 8. For this mode, a tolerance switch 50 is used where one side of switch 50 connects to ground and the other side selectively to pull up resistors 51 and 52 thereby connecting the microprocessor 28 to a voltage depending on whether the tolerance is to be stepped up or down by the operator. As discussed hereinabove, more than one set of color reference values can be stored.

Figure 5:
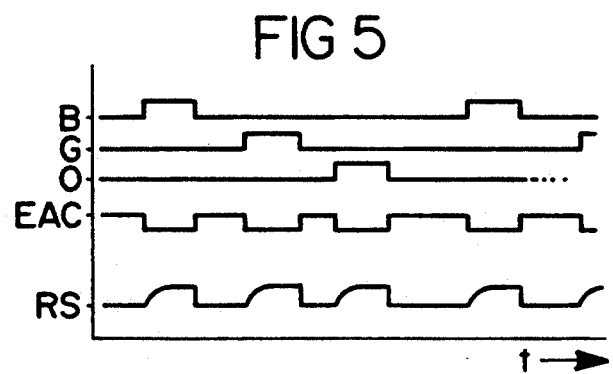
FIG. 5 illustrates a signal timing chart correlating various relationships within the present invention.
Figure 7:
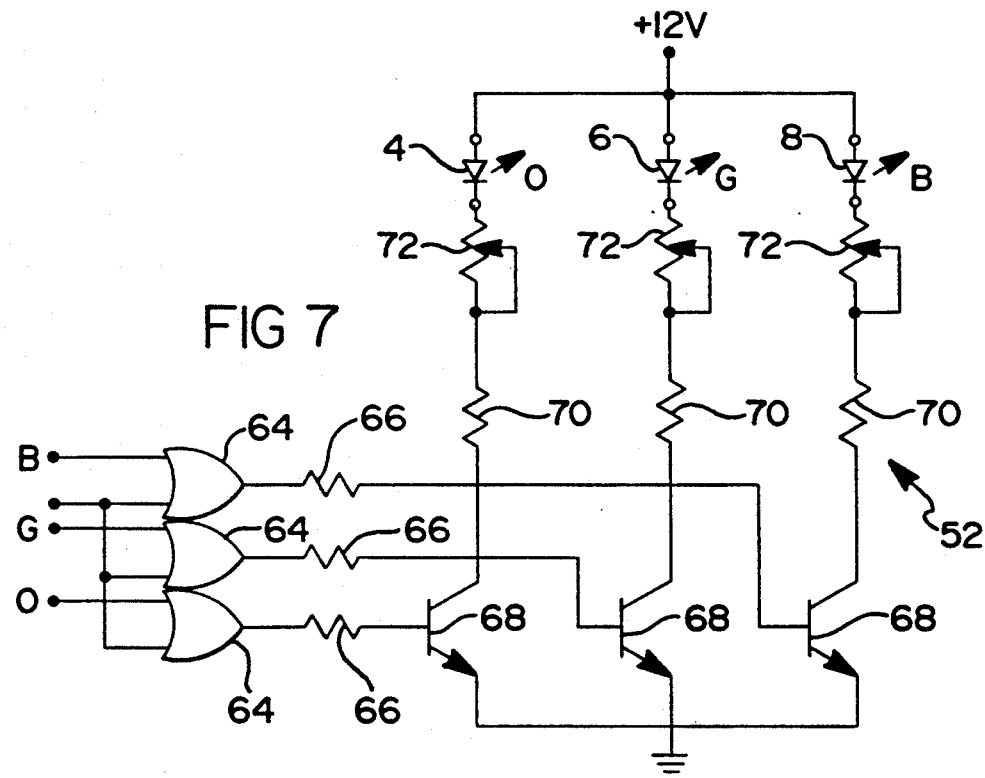
FIG. 7 illustrates a schematic diagram of an LED driver portion of a schematic of FIG. 6.

Blue, green and orange pulses from microprocessor 28 drive LED drive circuit 52 as shown in detail in FIG. 7 which can be adjusted to individually control the orange, green and blue LED currents through use of variable potentiometers 72 which are set and locked so that the output of the photodiode 102 is equal for all three illuminating colors when a Kodak Whitecard is used as object 18. The gain of the final op-amp 120 is controlled by way of digitally controlled potentiometer 121 which is established by the microprocessor 28 (FIG. 6). This adjustment compensates both for variations and light output versus current among the LEDs and for variations over the spectral range. Color sensor 1 is made substantially insensitive to steady state ambient light through the provision of an ambient compensating loop consisting of operational transconductance amplifier 108 and capacitor 122. Operational transconductance amplifier 108 functions as an amplifier only when enabled by the ambient compensation enable (EAC) signal shown in FIG. 5, which is true whenever none of the orange, green and blue LEDs 4, 6 and 8, respectively, are energized Otherwise, the output of the amplifier 108 is an open circuit which does not provide a discharge path for the voltage stored on capacitor 122. When amplifier 108 is enabled, a voltage is stored on capacitor 122 such that any current in photodiode 102 due to ambient light will be shunted away from amplifier 112. Capacitor 122 is large enough to retain this voltage during the signal measurement intervals when amplifier 108 is not enabled. The lower most signal trace in FIG. 6 represents the resultant sample (RS) signals received by microprocessor 28 from amplifier 120. The ambient compensation enable (EAC) signal (see FIG. 5) is generated by microprocessor 28 and turns off the ambient compensation provided by op amp 108 when any of the LEDs 4, 6, or 8 are illuminated.

The balance of the componentry illustrated in FIGS. 6 and 7 are listed hereinbelow, it being understood that they represent only one of any number of variants upon the representative invention inventive concept.

| REFERENCE NUMBER | TYPE | VALUE/TYPE |
| --- | --- | --- |
| 28 | Microprocessor | BGHCC11 |
| 4 | LED (orange) | HAA5066X (Stanley) |
| 6 | LED (green) | HGB5066X (Stanley) |
| 8 | LED (blue) | BLUE 470 (CREE) |
| 51 | Resistor | 10 K ohm |
| 52 | Resistor | 10 K ohm |
| 64 | OR Gate | CD4081 |
| 66 | Resistor | 1 K ohm |
| 68 | Transistor | 2N3904 |
| 70 | Resistor | 220 ohm |
| 72 | Potentiometer | 2 K ohm |
| 100 | Capacitor | 1 μf |
| 101 | Resistor | 10 K ohm |
| 102 | Photodiode | S1223-01 (Hamamatsu) |
| 103 | Resistor | 1 M ohm |
| 104 | Resistor | 7.5 K ohm |
| 105 | Resistor | 7.5 K ohm |
| 106 | Op Amp | 2N3906 |
| 107 | Resistor | 4.3 K ohm |
| 108 | Op Amp | CA3080 |
| 109 | Resistor | 1 K ohm |
| 110 | Resistor | 2 K ohm |
| 111 | Resistor | 50 K ohm |
| 112 | Op Amp | MC33282 |
| 113 | Resistor | 2.2 M ohm |
| 114 | Capacitor | 1 pf |
| 115 | Capacitor | 1 pf |
| 116 | Resistor | 510 K ohm |
| 117 | Op Amp | MC33282 |
| 118 | Resistor | 2 K ohm |
| 119 | Resistor | 10 K ohm |
| 120 | Op Amp | MC 34080 |
| 121 | Digital Variable Resistor | Xicor X9104S (100 K ohm) |
| 122 | Capacitor | 0.1 μf |

Figure 8:
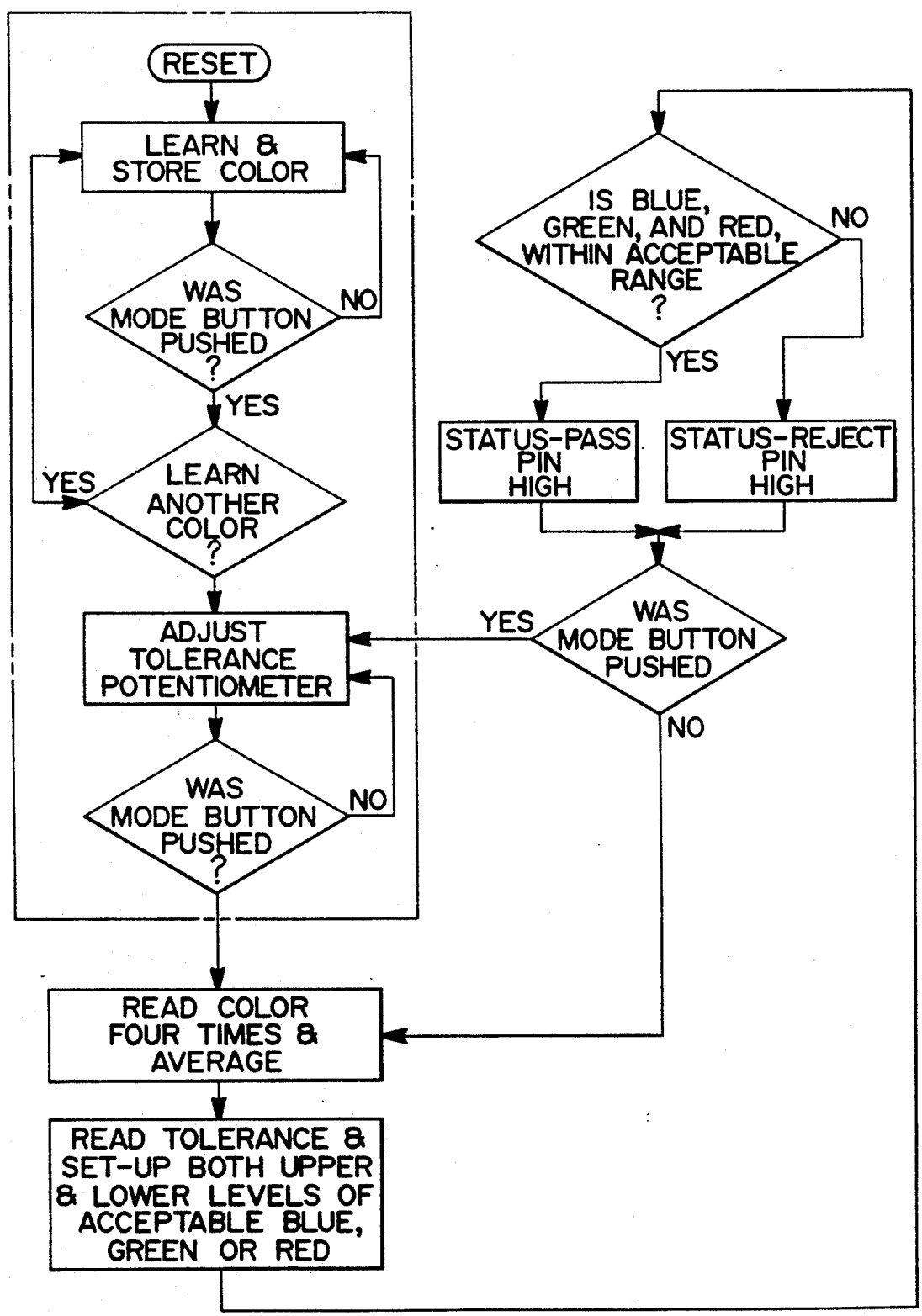
FIG. 8 illustrates a simplified flow chart of software implemented in the microprocessor of the present invention.

Referring to FIG. 8, the basic logic program within microprocessor 28 is illustrated. Microprocessor 28 adds intelligence and versatility to the color sensor system 1 in a way that would be difficult to achieve by discrete means such as though programmable logic devices. The microprocessor 28 performs three general tasks in the operation of the color sensor system 1. (1) it maintains control of the emitting LEDs 4, 6, 8 and the receiving photodiode 102; (2) it provides input analysis and response to the collected sensor data; (3) it manages local and remote communication interfaces. These functions are primarily originated by software driven inputs and outputs from the microprocessor 28. Each of these functions are expounded upon below.

The first sensor control task (1) is provided by software algorithms which switch the orange, green and blue LEDs 4, 6, and 8 on and off if a proper order in conjunction with the inversion of the EAC signal. Routines are also available for a programmable gain control on the receiving input amplifier, thus allowing for self calibration, in order to adjust to target applications of varying reflective gains. The routine attempts to achieve a linear but maximal gain for all three hues without driving the receiving amplifier into saturation for any individual hue. Circuitry and software is in place to provide an interrupt mechanism which permits triggering of the sensor readings based upon target presence or relative position in the sensor field of view. Initiation of this triggering mechanism can be accomplished through remote or local programming. There are several pushbottons on the sensor that are interpreted by the microprocessor. The mode button is a multipurpose control switch for progressing the sensor operation from a learn-color mode to the normal run mode of operation. In particular, the first push of the mode button out of reset will learn the color in the sensor view, another push will cause it to learn the second color if the device has been previously configured for more than one color. After learning colors the next push puts in the tolerance setting mode, and the next would put it in the normal run mode. If the mode button is pushed in the run mode, the device again returns to the tolerance set mode.

The second task (2) of the microcomputer 28 is for data analysis for color determination. After measuring the analog input and converting it to digital information, one of several paths can be taken to analyze the data, based on user preconfigured settings. The input readings may or may not be averaged, the choice being determined by how much response speed versus noisy signal suppression that is desired. Averaging slows the response time of the device but increases repeatability in the color determination. The readings may or may not be normalized, that is where each individual hue or LED light reflection reading is expressed as a ratio of the total of all three hue readings. The chief consequence of dealing with absolute rather than normalized voltage values for hue is that it renders the analysis more susceptible to variations in intensity of the reflected light due to sensor-to-target distance variation; this is not a problem when normalized. However, if the intensity of the reflected light can be held relatively constant, absolute readings will distinguish different tones of the same color hue, while normalizing masks the distinction. One-color or multi-color sensing can be selected by dip switch or remote terminal programming as well. In the current design, the output of the color analysis is made up of two go/no-go control lines which provide a go/no-go signal or a more sophisticated process control analysis can be performed on the digitized output. One line signals high for a passing color, the other for a failure of the color match to the stored standard. Each line has a corresponding LED indicator for demonstrating purposes. When there is a match to any stored color, the go-signal pin signals. Plug-in external sensors may serve as marker inputs to distinguish which color is being tested at a given time (mentioned above as part of the triggering mechanism).

The third task (3) incorporates the elements of the user interface. Simple interface elements are provided such as the reset button, which restarts the device and sets it in the learn color mode. The second button is the mode button, which as described above, progresses the device operation sequentially through the available modes. LED indicators under the control of the microprocessor, distinguish the state of the device operation. These indicators are the learn versus run mode, color good versus bad, learn color versus tolerant set mode, first color or second color learn, and power-on LEDs. User defined set-up configurations can be entered in two ways. The operating configuration can be set by either on board switches or remote programming located on the sensor (local) or by serially communicating to the sensor from a (remote) personal computer or dumb ASCII terminal. Serial communication software is available in the microcomputer chip coding. Serial communication can be initiated during the run mode which will return the operating state to the learn mode.

A more detailed description of this approach is contained in U.S. patent application Ser. No. 07/378,570 filed on Jul. 11, 1989, allowance granted on Jan. 22, 1991, and issued as U.S. Pat. No. 5,021,645 on Jun. 4, 1991, the disclosure of which is incorporated herein by reference. An alternative control/processor approach is described in U.S. Pat. No. 4,917,500.

Once again referring to FIG. 1, the transmitting section 2 and receiving section 22 can be packaged together and mounted at a remote location away from the process that is to be controlled. Optical fiber bundles 10, 12 14 and 20 allow the electronics portion of the present invention to be remotely mounted for convenience and isolation from a harsh environment while the sensor end 16 is positioned relatively close to the object 18 whose color is to be measured. Communication line 31 is connected to a read out means such as another computer that interprets the signal and controls the process or can be directly connected to a data logger or a process line stop/go switching device. Lenses can be placed inbetween the object 18 and the sensing end 16 to enhance the optical qualities of the measurement.

Figure 2:
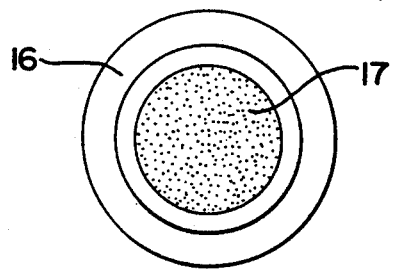
FIG. 2 illustrates an end view of a sensing end of the present invention taken on line II—II in FIG. 1

Now referring to FIG. 2, an end view of sensing head 16 is shown with the individual optical fiber terminated ends which are randomly mixed so that bundles 10, 12, 14 and 20 are substantially distributed throughout the area 17 of the end of the sensing head 16.

Figure 3:
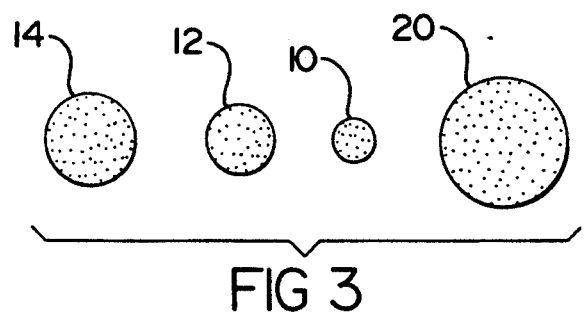
FIG. 3 illustrates a cross-sectional view taken on line III—III in FIG. 1 of three transmitting and one receiving optical fiber bundle prior to randomization into a single system bundle leading into the sensing end of FIG. 2.

FIG. 3 shows a section of each of the transmitting optical fiber bundles 10, 12, and 14 where the differing diameters is clearly shown (the sheathing is not shown). Optical fiber bundle 14 which carries the light output from the blue LED 8 is sized with a diameter of approximately 0.125 inch where the optical fiber bundle 12 which carries the light output from the green LED 6 has a diameter of approximately 0.11 inch and optical fiber bundle 10 which carries the light output from the orange LED 4 has a diameter of approximately 0.07 inch. The purpose of the differing diameters is to most efficiently use the area of the fiber to transmit and receive light energy. The output of the blue LED 8 is approximately 21% that of the orange LED 4 while the green LED 6 has a light energy output that is approximately 38% of that of the orange LED 4. The optical fiber used is similar to that available from Cuda Products as single bundles under Part No. CS062 which are four-furcated with a stainless steel sheathing. The single fibers that make up each of the optical fiber bundles 10, 12, 14 are grouped to form a single system bundle 15 where all of the single fibers are longitudinally randomized so that each fiber's postition relative to one another changes along the length of the single system bundle 15.

The transmissibility of the optical fiber varies with the wavelength of the transmitted light which also can effect the accuracy of the color measurement. The differing diameters of the optical fiber bundles 10, 12 and 14 also take this effect into account and are sized to mitigate the variance in transmissibility as well as the LED output. The diameter of an optical fiber bundle can be increased to offset a general loss where an optical fiber bundle with a larger diameter has a greater light receiving capability from an LED. In addition, the diameters are sized to offset the effect of the spectral response of the light sensitive photodiode 24 located in receiving section 22. The overall effect is that the optical fiber bundles 10, 12, and 14 are sized in diameter so that the output electrical signal from the receiver light sensitive photodiode 24 is equal for each LED pulse when a Kodak Whitecard is used for object 18.

More specifically, the optical fiber bundles 10, 12, and 14 consist of a plurality of individual optical fibers. The diameter of each bundle is sized according to the light power output of its associated LED, the transmission loss of the optical fiber bundle and the spectral response of the light sensitive photodiode 24. For example, the following parameters can be used to size the optical fiber bundle:

| LED Color | Orange | Green | Blue |
|---|---|---|---|
| Power (µW) | 72 | 27 | 15 |
| Fiber Transmission Loss (%) | 89 | 87 | 83 |
| Light Output Ratio | 1 | 2.6 | 4.5 |
| Light Detector Response Ratio | 0.35 | 0.29 | 0.2 |
| Selected Bundle Diameter (in) | 0.070 | 0.110 | 0.125 |
| Bundle Area (in$^2$) | $1.5 \times 10^{-2}$ | $3.8 \times 10^{-2}$ | $4.9 \times 10^{-2}$ |
| Area Ratio | 1.0 | 2.5 | 3.3 |

As evidenced using this scheme, the area (area ratio) of the bundle approximately corresponds to the fiber transmission loss multiplied by the light output ratio of the LEDs multiplied by the light detector response ratio so that the amount of light transmitted through each bundle 10, 12, or 14 is optimized so that the output of the photodiode 24 for each of the LEDs 4, 6, and 8 generated colors is equal when a Kodak Whitecard is used as a target object 18.

Figure 4:
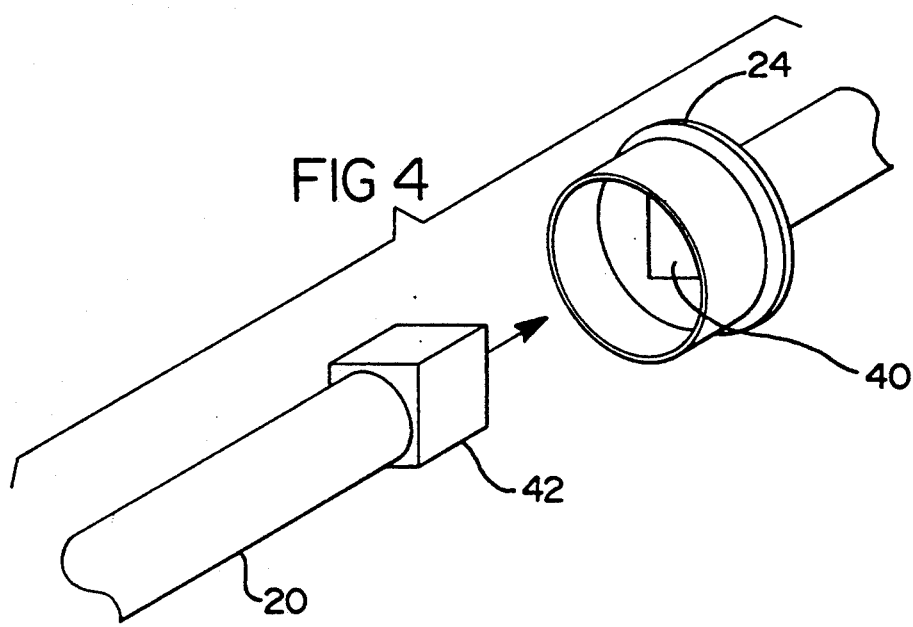
FIG. 4 illustrates a perspective view of a receiving optical fiber bundle and the input section of the PIN photodiode of the present invention.

FIG. 4 shows a perspective view of the photo sensitive device 24 such as a PIN type Photodiode available from Hamamatsu as Part No. S1223-01 where the input section 40 has a particular configuration that is matched by the termination of the receiving optical fiber bundle 20 as shown by the cube shaped termination 42. In this manner, the signal to noise ratio of the receiving section 22 is maximized. The individual optical fibers of the optical fiber bundle 20 are randomized and displaced to fully occupy the cube shaped termination 42.

Figure 9:
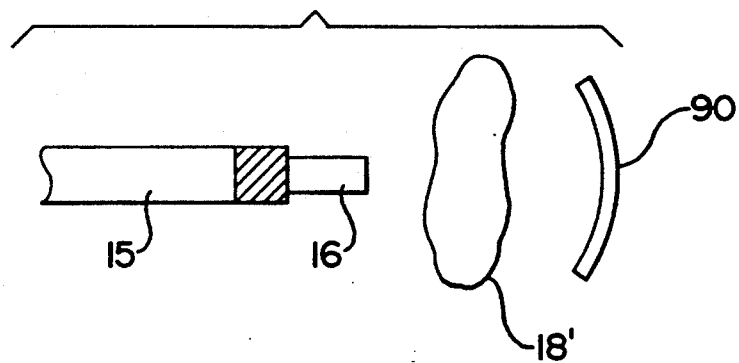
FIG. 9 illustrates a schematic diagram of the preferred embodiment of the present invention used with a reflecting mirror.

Now referring to FIG. 9, what is schematically illustrated is a method to utilize the present invention to measure the color content of a translucent object 18' such as a fluid. A mirrored surface 90 is located relative to the sensing end 16 so that the object 18' lies between the mirrored surface 90 and the sensing end 16. The mirrored surface 90 can be the type known as a concave mirror with a curvature that reflects the transmitted light (produced at the sensing end 16 which travels through the translucent object 18') so that it once again travels through the object 18' and then into the receiving fiber optic bundle 20 which has been randomized in the sensing end 16 and directed into the receiving section 22 for processing. In this manner, the color characteristics of a translucent object 18' such as a fluid can be more accurately measured.

Figure 10:
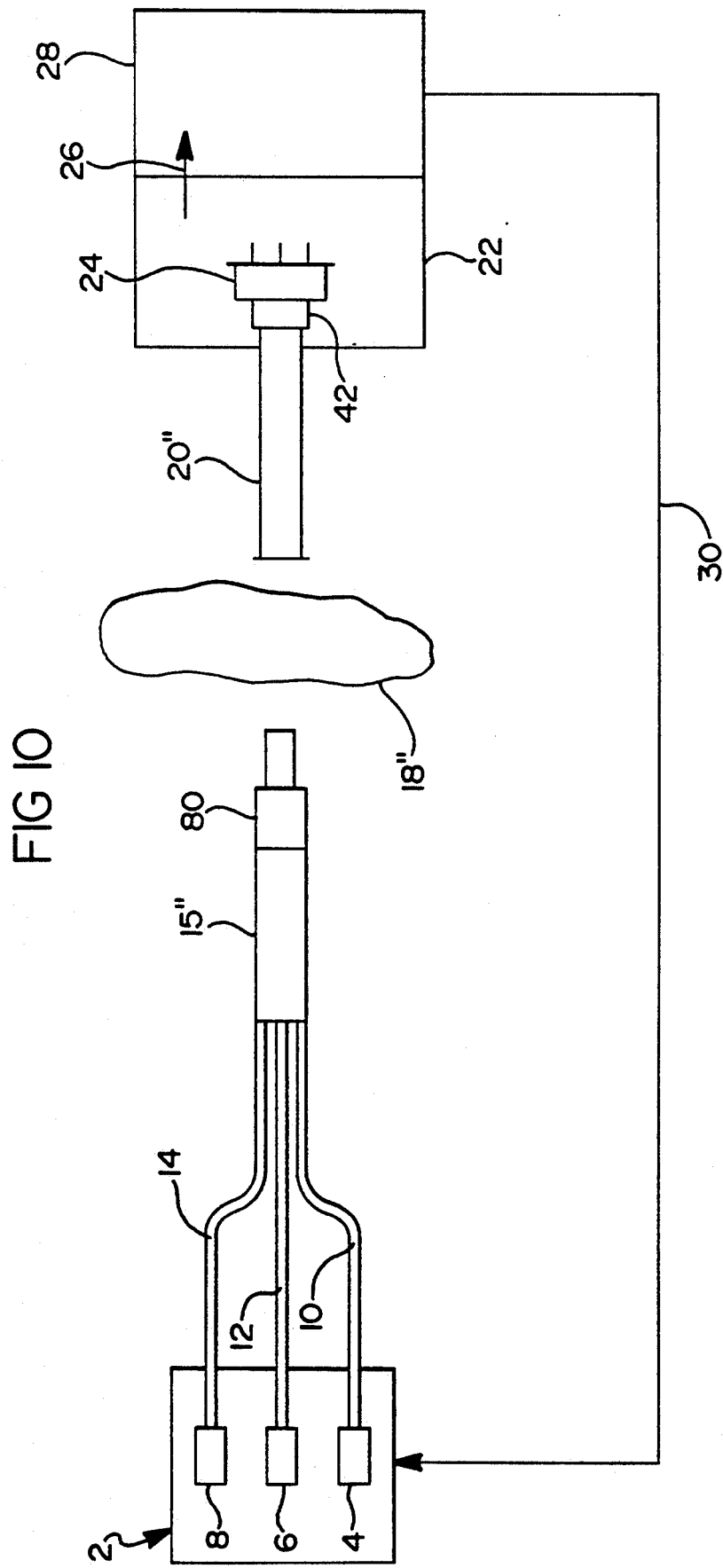
FIG. 10 illustrates a schematic of an alternative embodiment of the present invention where the receiving and transmitting fiber optical bundles are separated.

FIG. 10 illustrates an alternate method of measuring the color characteristics of a translucent object 18'' where the receiving optical bundle 20'' is separated from the transmitting optical bundles 10, 12, and 14 and positioned directly opposed to the emitting end 80, (Since the receiving bundle 20 is no longer a part of the single system bundle 15, the transmitting optical fiber bundles 10, 12 and 14 are combined and randomized in a single system bundle 15'' and terminate with an emitting end 80). The translucent object 18' is placed between the emitting end 80 and the termination of the receiving optical fiber bundle 20''. In this manner, the light emitted by the fibers at the emitting end 80 passes through the translucent object 18'' and is then conducted by the receiving optical bundle 20'' to the matching input section 42 of the light sensitive photodiode 24 in the receiving section 22. The signal from the photodiode is conducted to the microprocessor 28 and is then processed as described supra. The transmitting section 2 can be physically separated from the receiving section 22 with electronics communication via line 30.

Thus, there has been shown and described a novel color sensing system which overcomes the limitations of the prior art and fulfills all of the objects and advantages enumerated herein. Many changes, modifications, variations and other uses and applications of the subject invention will become apparent to those skilled in the art after considering the specification and the accompanying drawings which disclose a preferred embodiment thereof. All such changes, modifications, variations and other uses and applications which do not depart from the spirit and scope of the invention are deemed to be covered by the invention which is limited only by the claims which follow.

What is claimed is:

1. A color sensing system for the recognition of a colored object comprising:
   a plurality of electronic light emitters, each emitting light in a predetermined narrow-band range of wavelengths;
   a receiving randomized optical fiber bundle having a first and second end for conducting a reflected light from a colored object; said first end directed at said colored object;
   an electronic light receiver means coupled to said second end of said receiving randomized optical fiber bundle for converting said reflected light into an electrical signal; and
   a plurality of light transmitting randomized optical fiber bundles, each bundle coupled to a respective one of said light emitters and having a cross-sectional area approximately inversely proportional to the product of a light power level of said respective light emitter multiplied by the spectral response of said electronic light receiver, said emitting light conducted through said transmitting randomized optical fiber bundle and illuminating said colored object causing light to be reflected therefrom where said transmitting randomized optical fiber bundle is substantially constant in effective cross-sectional area over its length; and
   an electronic processing means connected to said electronic light receiver means for making a color recognition determination based on said electrical signal.

2. The color sensing system according to claim 1, wherein said electronic light emitters are light emitting diodes.

3. The color sensing system according to claim 2, wherein said diodes are selected having one emitting light with a peak wavelength of approximately 605 nm, one emitting light with a peak wavelength of approximately 555 nm, and one emitting light with a peak wavelength of approximately 470 nm.

4. The color sensing system according to claim 1, wherein said transmitting randomized optical fiber bundles have cross-sectional diameters approximately in the ratio of 1:1.5:1.8 respectively connected to an orange, green and blue electronic light emitter of the type known as light emitting diodes.

5. The color sensing system according to claim 1, wherein said electronic light receiver means is of the type using a PIN photodiode, said receiving randomized optical fiber bundle having said second end shaped to match an input receptacle to said PIN photodiode.

6. The color sensing system according to claim 1, wherein an optical lens is placed between said colored object and said first end.

7. The color sensing system according to claim 1, wherein said receiving randomized optical fiber bundle is joined to and randomized with said light transmitting randomized optical fiber bundles.

8. The color sensing system according to claim 1, wherein said transmitting randomized optical fiber bundles and said receiving randomized optical fiber bundles are formed of a plurality of randomized single optical fiber strands, said transmitting randomized optical fiber bundles and said receiving randomized optical fiber bundles are separate and then joined by intermixing and randomizing said fiber strands forming a single optical fiber bundle having a substantially constant cross-sectional area and having an end directed at said colored object.

9. A color sensing system for the recognition of colored objects, comprising:
   at least two light transmitters each emitting light in a predetermined narrow-based range of wavelengths;
   light receiving means for receiving reflected light from the colored object and converting said reflected light into individual electrical signals;
   at least two transmitting randomized optical fiber bundles each having a first end converted to a respective light transmitter and a second end directed at the colored object said bundles conducting said emitting light from said first end to said second end and emerging from said second end to illuminate the colored object where each of the said transmitting randomized optical fiber bundles has an approximately constant diameter approximately in inverse proportion to the light output power of said light transmitter and where each of said transmitting randomized optical fiber bundles has an approximately constant effective cross-sectional area;
   a receiving randomized optical fiber bundle having a first end directed at the object and a second end directed as said light receiving means; and
   signal processing means coupled to said individual electrical signals for generating an output signal representative of the colored surface of said object.

10. The color sensing system according to claim 9, wherein said electronic light transmitters are light emitting diodes, said diodes selected to transmit light in a narrow-band range of wavelengths.

11. The color sensing system according to claim 9, wherein said light receiver comprises a light sensitive semiconductor where said second end of said receiving optical fiber bundle is shaped to match the shape of an input section of said light sensitive semiconductor.

12. The color sensing system according to claim 11, wherein said light sensitive semiconductor is a PIN photodiode.

13. The color sensing system according to claim 9, wherein said second ends of said transmitting randomized optical fiber bundles and said second end of said receiving randomized optical bundle are comprised of a plurality of optical fibers which are randomized in a sensing end.

14. The color sensing system according to claim 9, wherein said cross-sectional area is further sized to offset a difference is light transmission loss of said transmitting randomized optical fiber bundle.

15. The color sensing system according to claim 9, wherein an optical lens is interposed between said first end of said receiving randomized optical fiber bundle and the object.

16. The color sensing system according to claim 9, wherein said first end of said receiving randomized optical fiber bundle is grouped in a package with said second end of said transmitting randomized optical fiber bundles and a reflective surface is placed opposite said package with the colored object therebetween, said reflective surface positioned to reflect a portion of said emitting light passing through said colored object back through said colored object and into said first end of said receiving randomized optical fiber bundle.

17. The color sensing system according to claim 9, wherein said second ends of said transmitting randomized optical fiber bundles are positioned opposing said first end of said receiving randomized optical fiber bundle, a colored object being placed therebetween.

18. The color sensing system according to claim 9, wherein said transmitting randomized fiber bundles have a cross-sectional area in proportion to the spectral response of said light receiving means.

* * * * *